(12) United States Patent
Tokuda et al.

(10) Patent No.: US 11,324,763 B2
(45) Date of Patent: May 10, 2022

(54) MALARIA TRANSMISSION PREVENTION AGENT HAVING RARE SUGAR AS EFFECTIVE COMPONENT THEREOF AND MALARIAL PARASITE GROWTH REGULATING AGENT

(71) Applicants: NATIONAL UNIVERSITY CORPORATION KAGAWA UNIVERSITY, Takamatsu (JP); MATSUTANI CHEMICAL INDUSTRY CO., LTD., Itami (JP)

(72) Inventors: Masaaki Tokuda, Kagawa (JP); Meiji Arai, Kagawa (JP); Kazuhiro Okuma, Itami (JP)

(73) Assignees: National University Corporation Kagawa University, Takamatsu (JP); MATSUTANI CHEMICAL INDUSTRY CO., LTD., Itami (JP)

( * ) Notice: Subject to any disclaimer, the term of this patent is extended or adjusted under 35 U.S.C. 154(b) by 0 days.

(21) Appl. No.: 15/128,797

(22) PCT Filed: Mar. 20, 2015

(86) PCT No.: PCT/JP2015/058563
§ 371 (c)(1),
(2) Date: Sep. 23, 2016

(87) PCT Pub. No.: WO2015/146849
PCT Pub. Date: Oct. 1, 2015

(65) Prior Publication Data
US 2017/0100418 A1    Apr. 13, 2017

(30) Foreign Application Priority Data

Mar. 25, 2014  (JP) .............................. JP2014-062072

(51) Int. Cl.
*A61K 31/7004* (2006.01)

(52) U.S. Cl.
CPC ........... *A61K 31/7004* (2013.01); *Y02A 50/30* (2018.01)

(58) Field of Classification Search
CPC ................................................ A61K 31/7004
USPC ......................................................... 514/23
See application file for complete search history.

(56) References Cited

U.S. PATENT DOCUMENTS 5,141,925 A * 8/1992 Alroy ..................... A61K 31/70
514/20.9
5,166,193 A    11/1992 Levin et al.
5,370,873 A * 12/1994 Udeinya ................. A61K 36/58
424/761
5,763,442 A    6/1998 Medlen et al.
2008/0306011 A1 * 12/2008 Tokuda .............. A61K 31/7004
514/23

FOREIGN PATENT DOCUMENTS

| JP | 5-148140 A | 6/1993 |
| JP | 6-157308 A | 6/1994 |
| JP | 8-231401 A | 9/1996 |
| JP | 2001-278787 A | 10/2001 |
| JP | 2004-307428 A | 11/2004 |
| JP | 2008-1630 A | 1/2008 |
| JP | 2013-82639 A | 5/2013 |
| WO | 2007/100102 A1 | 9/2007 |

OTHER PUBLICATIONS

Bai et al. (Sheng wu gong cheng xue bao = Chinese journal of biotechnology, (Apr. 2012) vol. 28, No. 4, pp. 457-465).*
Nayar et al. (Comp. Biochem. Physiol. vol. 116B, No. 1, pp. 109-117).*
Manda et al. (Malaria Journal 2007, 6:113, pp. 1-11).*
Knowles et al. (Journal of General Microbiology (1978), 108, 17-25).*
Oaks et al. (Malaria: Obstacles and Opportunities; Washington (DC): National Academies Press (US); 1991, ISBN-10: 0-309-04527-4; 6 Parasite Biology).*
Lutgen (Malaria World; https://malariaworld.org/blog/glucose-and-malaria, Feb. 23, 2013 13:35).*
Matsuo et al. (J Clin Biochem Nutr. Sep. 2009; 45(2): 202-206).*
Kessler et al. (The Journal of Experimental Biology 216, 1292-1306).*
Takamine et al., "Manufacturing Method of Rare Sugar Syrup through Alkali Isomerization and its Inhibitory Effect of α-Glucosidase", Bulletin of Applied Glycoscience, 2015, 5(1), pp. 44-49, cited in Specification, w/English abstract (5 pages).
Sato et al, D-Ribose Competitively Reverses Inhibition by D-Psicose of Larval Growth in Caenorhabditis elegans, Biol. Pharm. Bull., 2009, vol. 32, No. 5, pp. 950-952, cited in ISR (3 pages).
Harada et al., D-Allose and D-psicose reinforce the action of metronidazole on trichomonad, Parasitol Res , 2012, vol. 110, pp. 1565-1567, cited in ISR (3 pages).

(Continued)

*Primary Examiner* — Shaojia A Jiang
*Assistant Examiner* — Michael C Henry
(74) *Attorney, Agent, or Firm* — WHDA, LLP

(57) ABSTRACT

Problem: A malaria transmission blocker or a malaria parasite growth inhibitor is provided as a result of finding a druq which inhibits malaria parasite growth in the body of a vector mosquito. Solution: A malaria parasite growth inhibitor or transmission blocker containing a rare sugar such as D-allose or D-psicose as an active ingredient.

3 Claims, 15 Drawing Sheets

(56) References Cited

OTHER PUBLICATIONS

International Search Report dated May 19, 2015, issued in counterpart International Application No. PCT/JP2015/058563 (1 page).
Third Party Observation dated Mar. 17, 2015, issued in counterpart International Application No. PCT/JP2015/058563 (2 pages).

* cited by examiner

[fig.1]
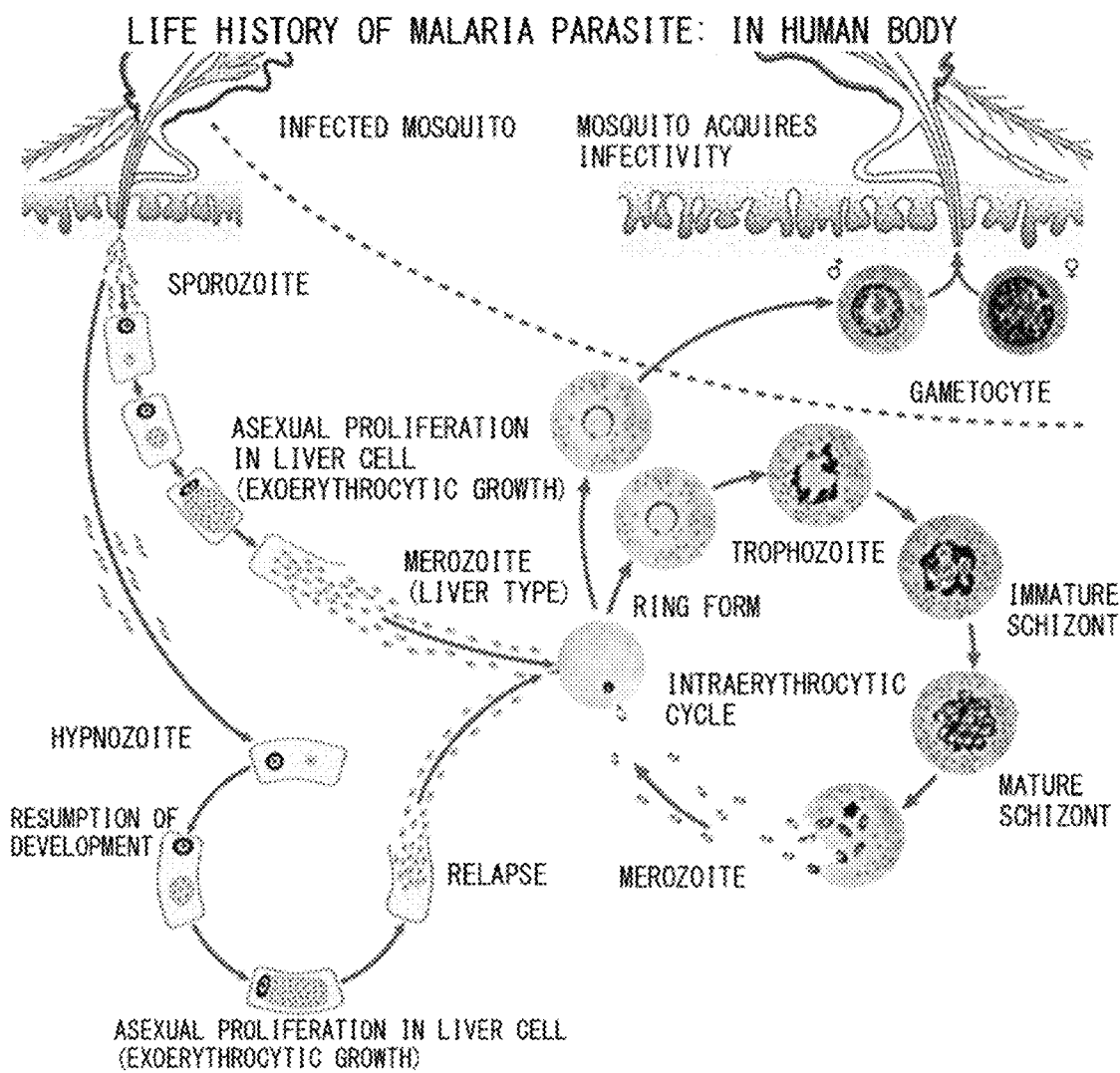

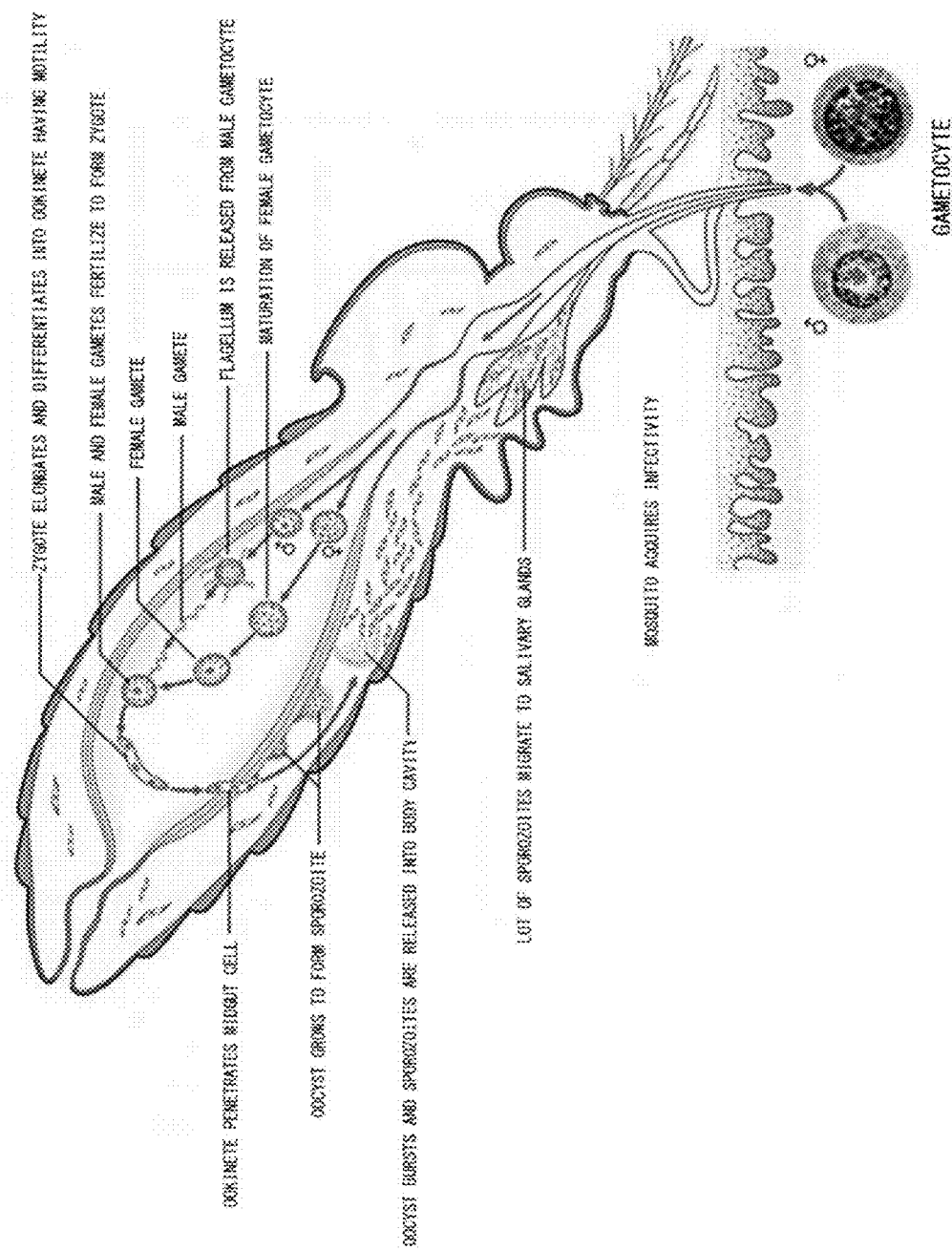

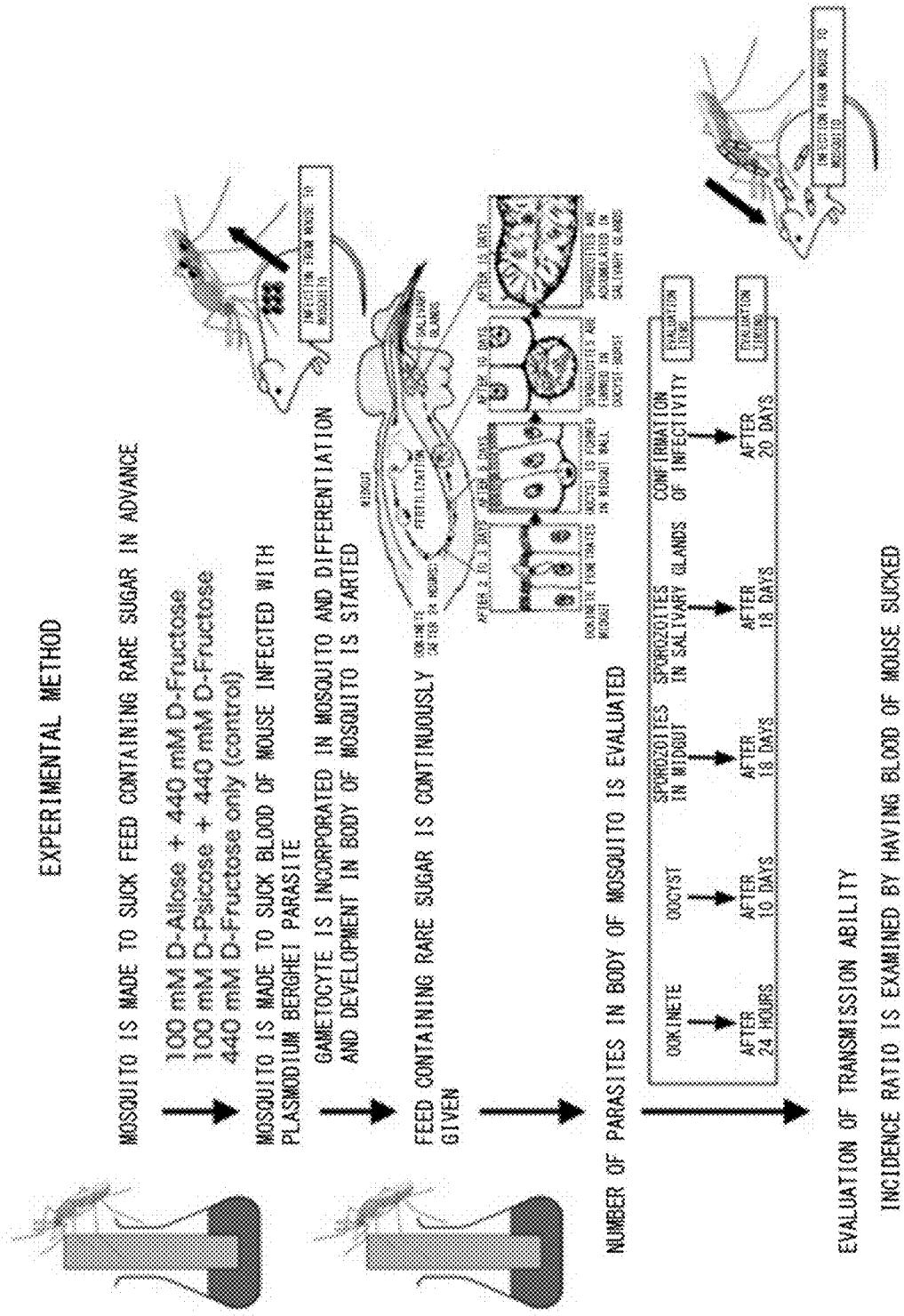

[fig.4]
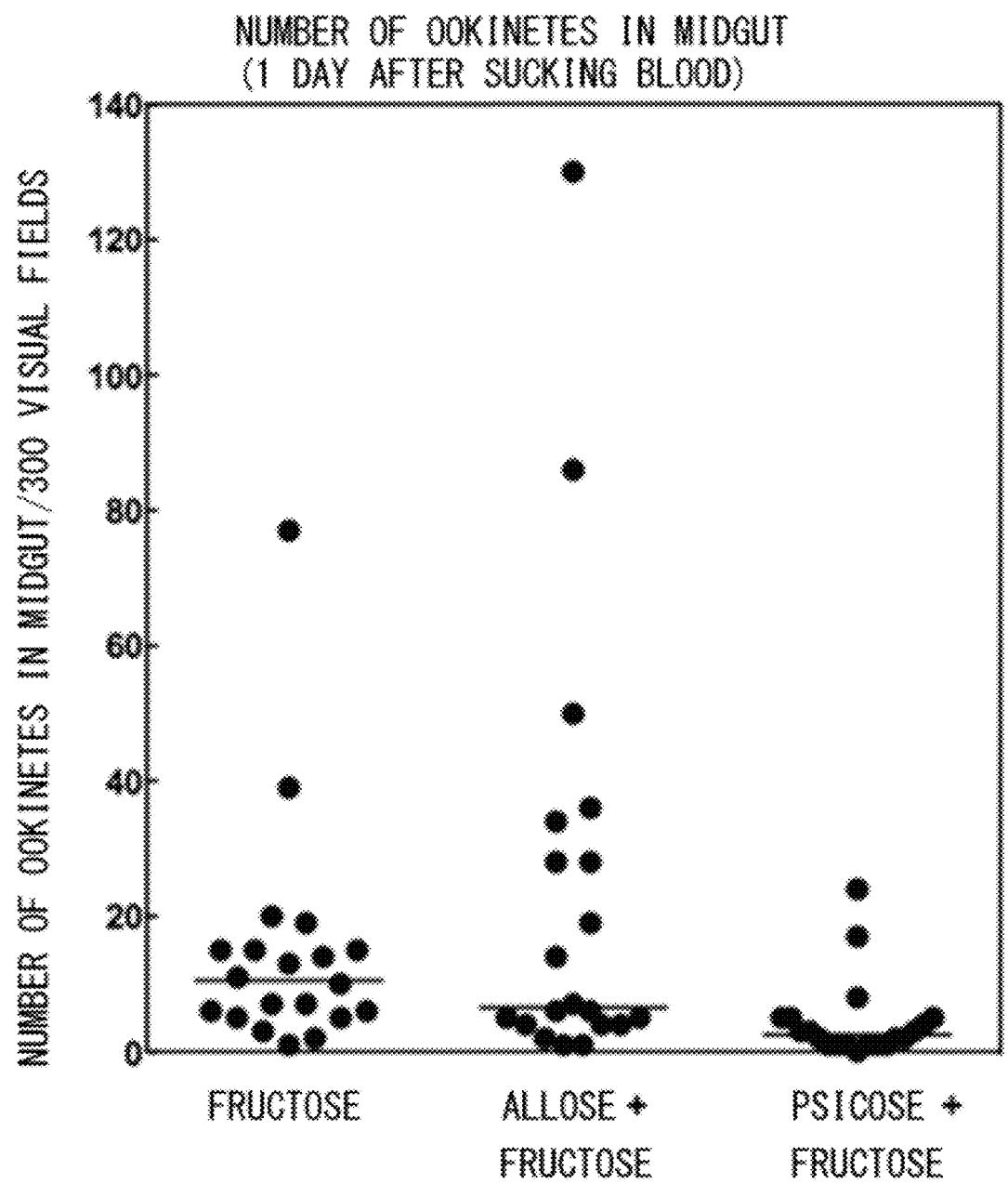

[fig.5]
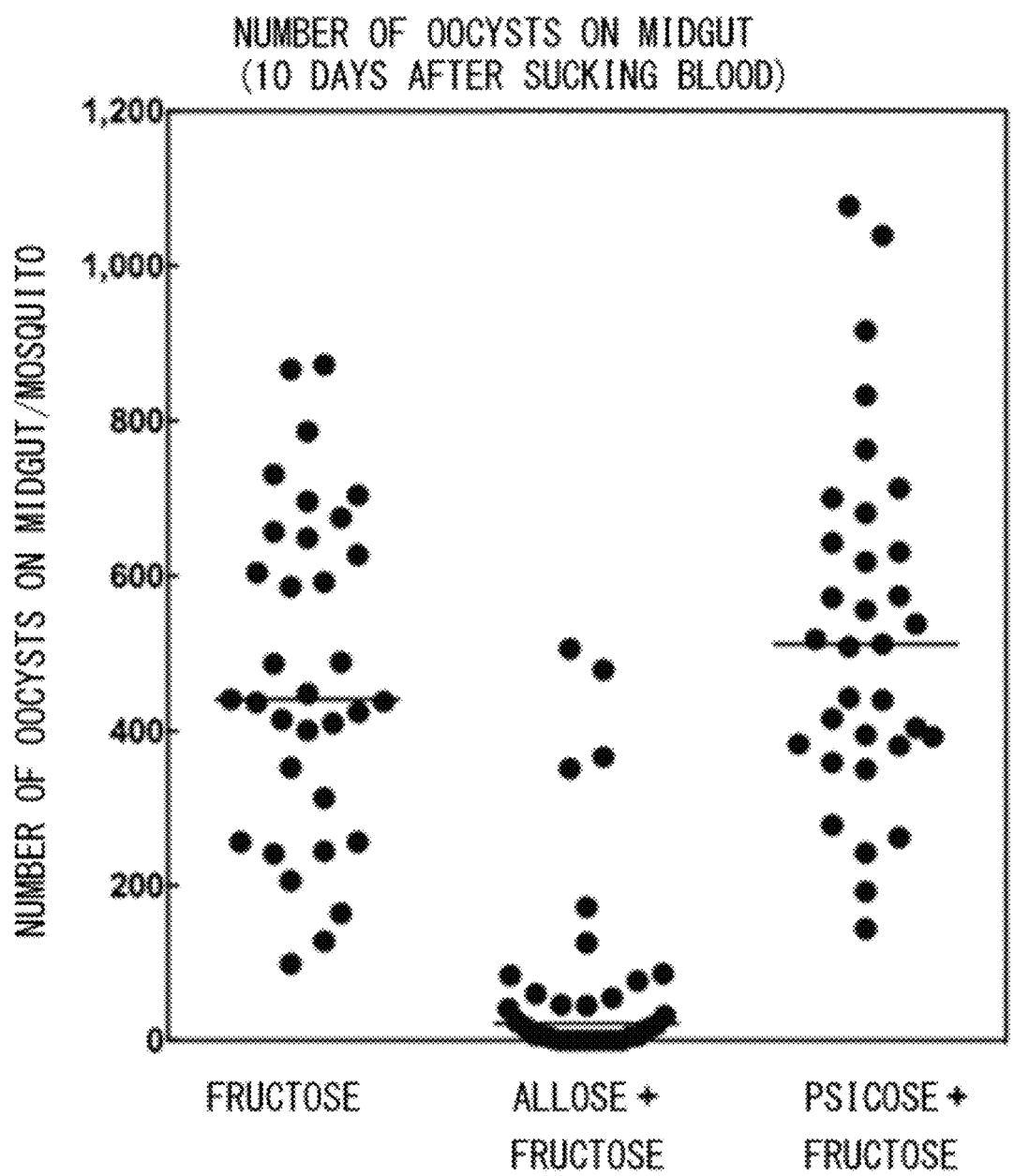

[fig.6]
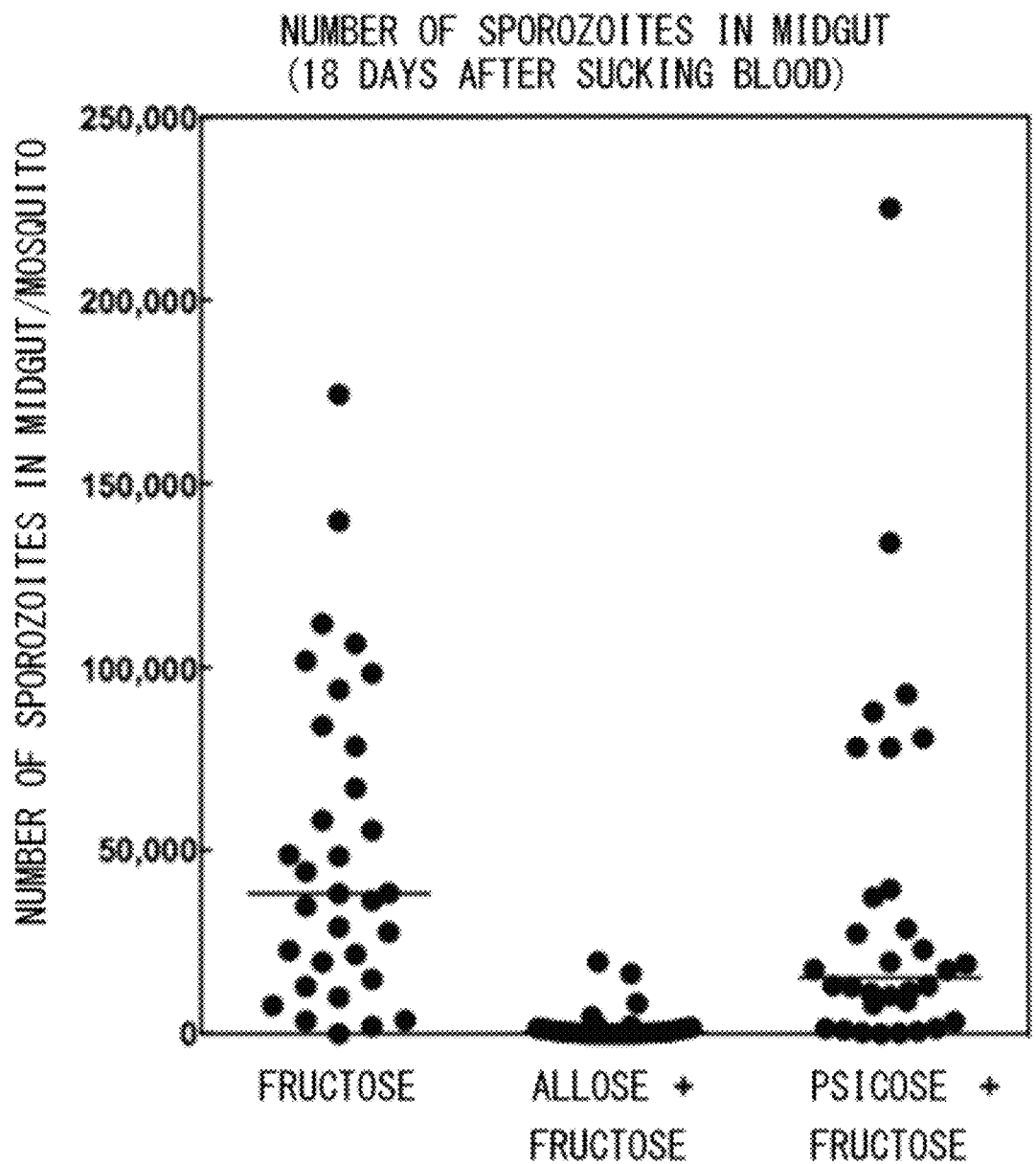

[fig.7]
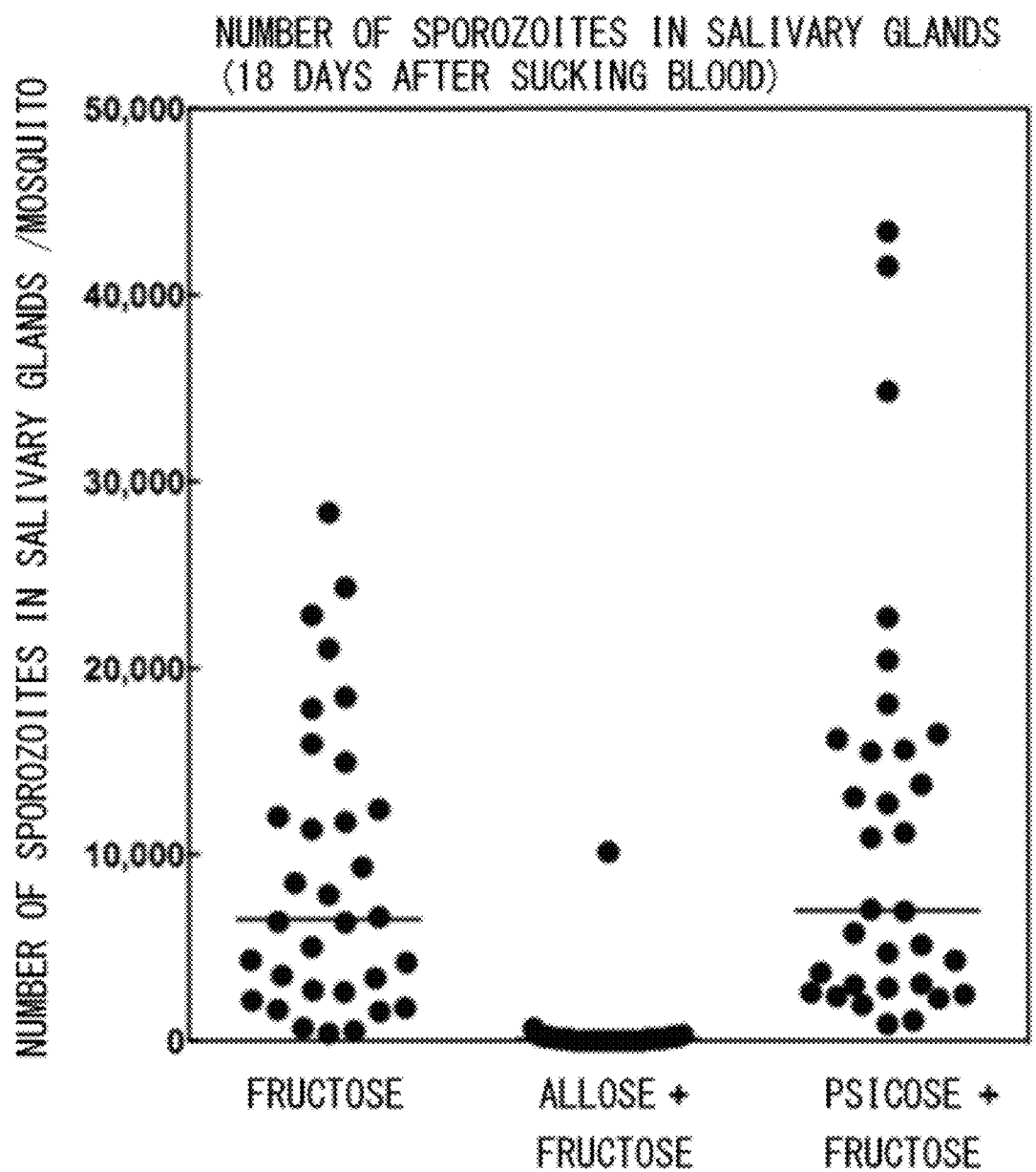

[fig.8]
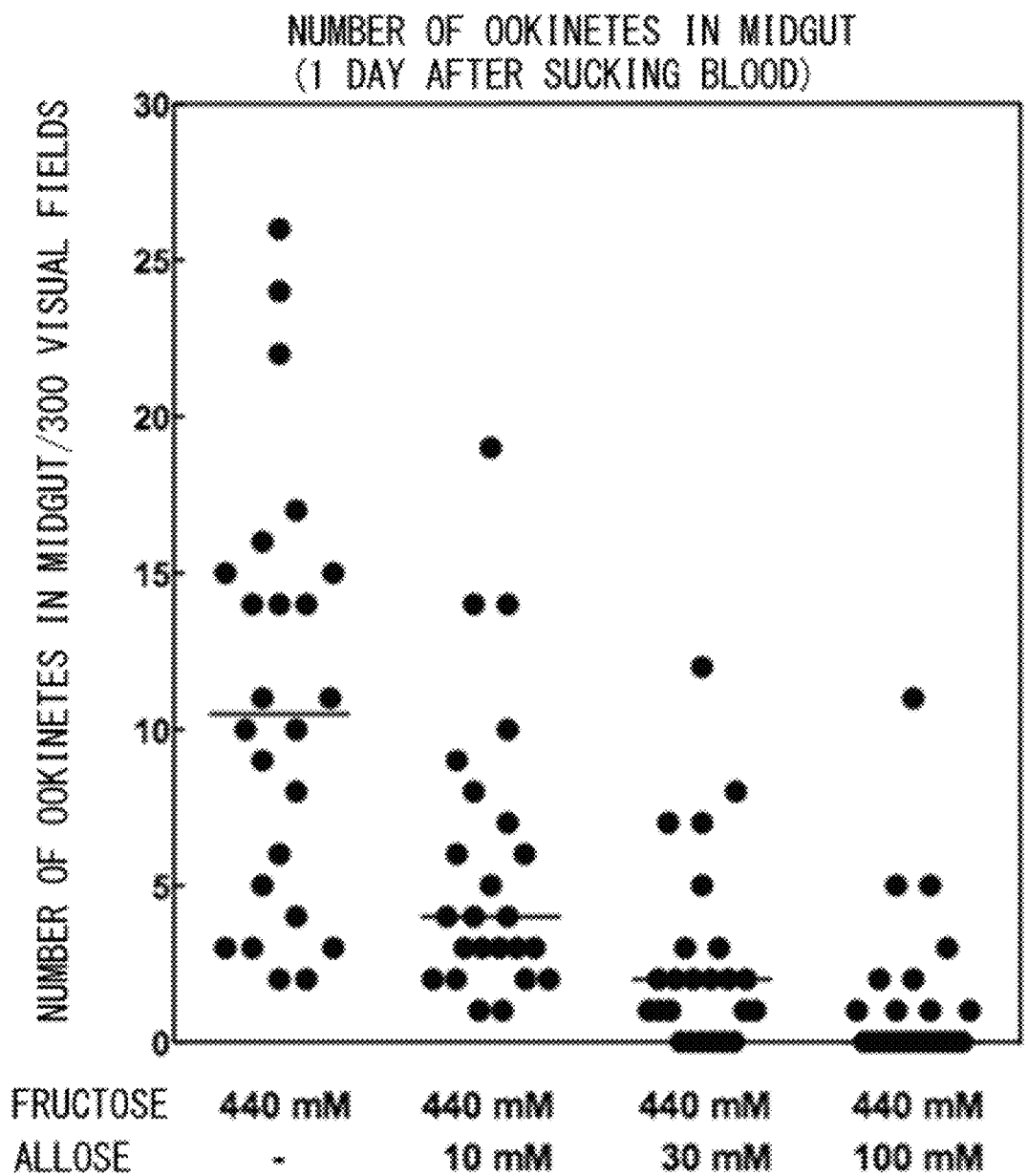

[fig.9]
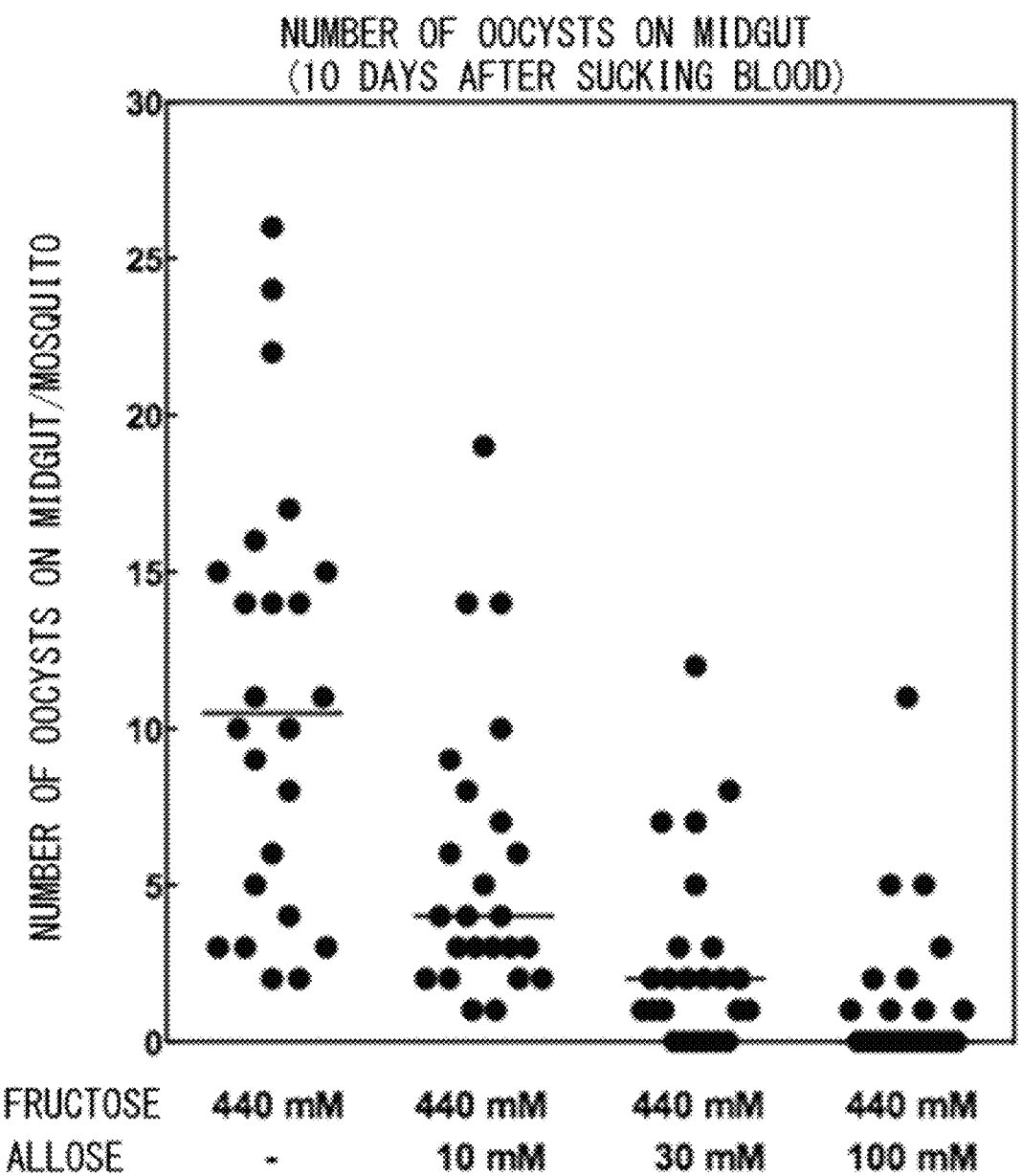

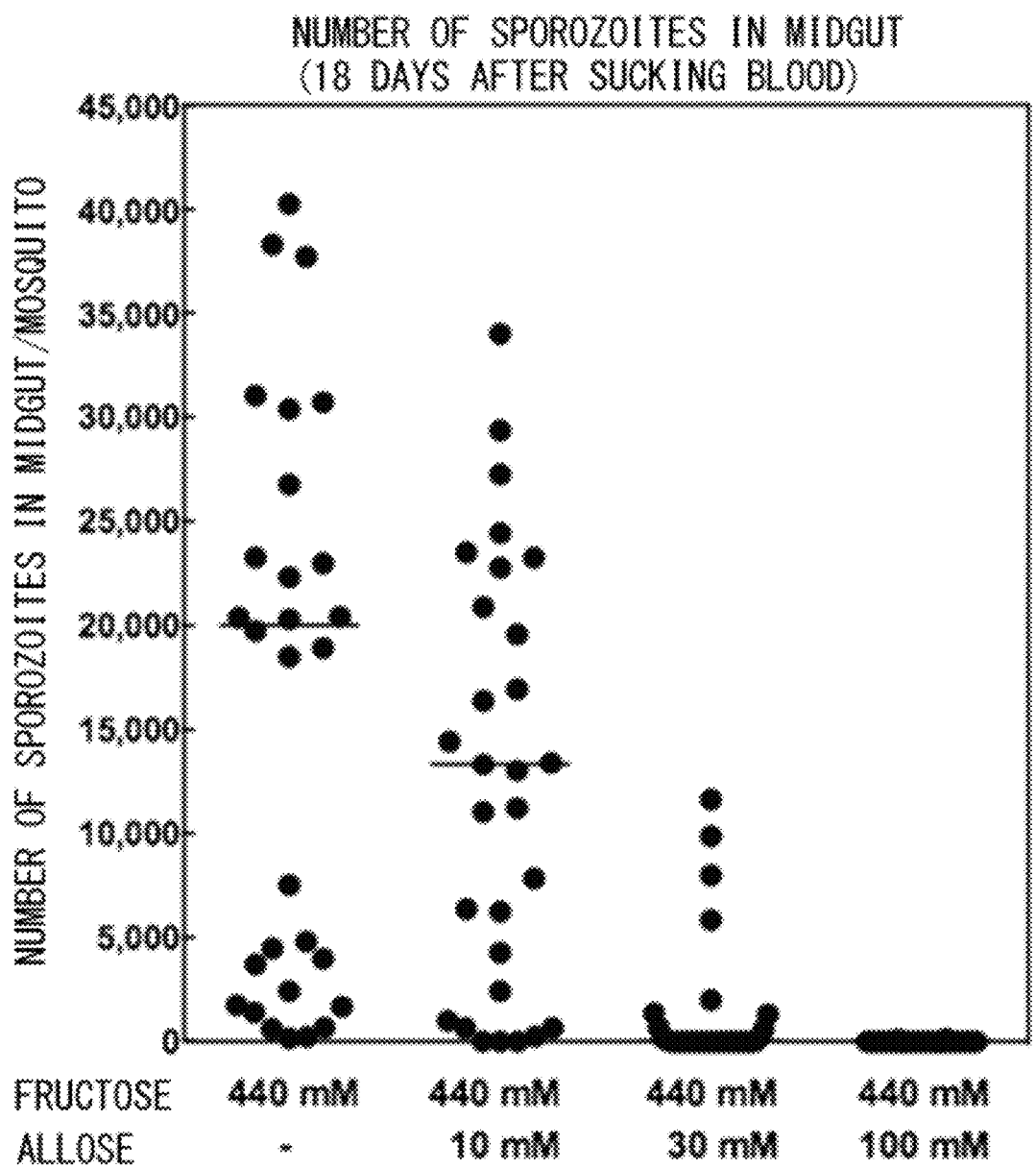

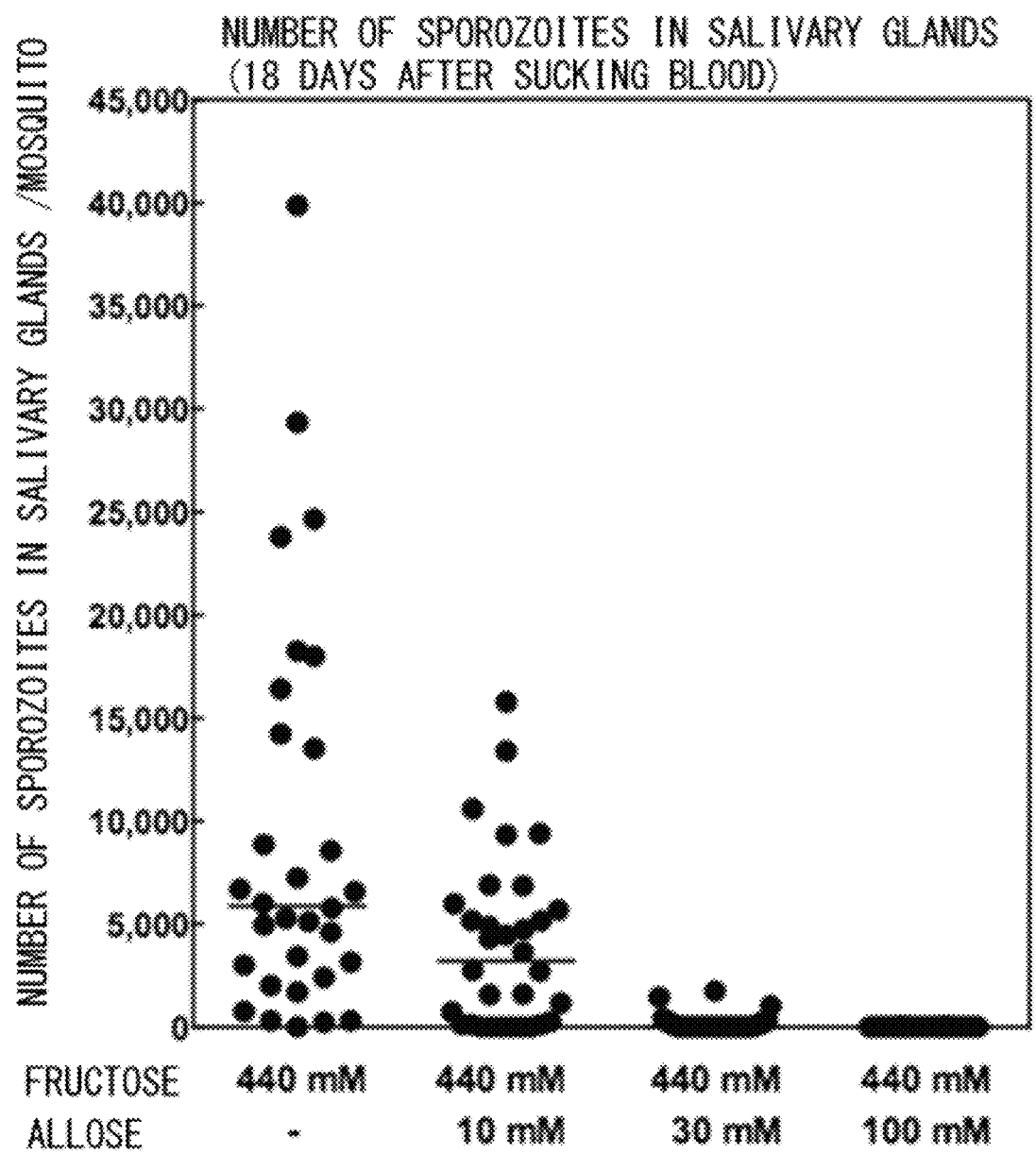
[fig.11]

[fig.12]
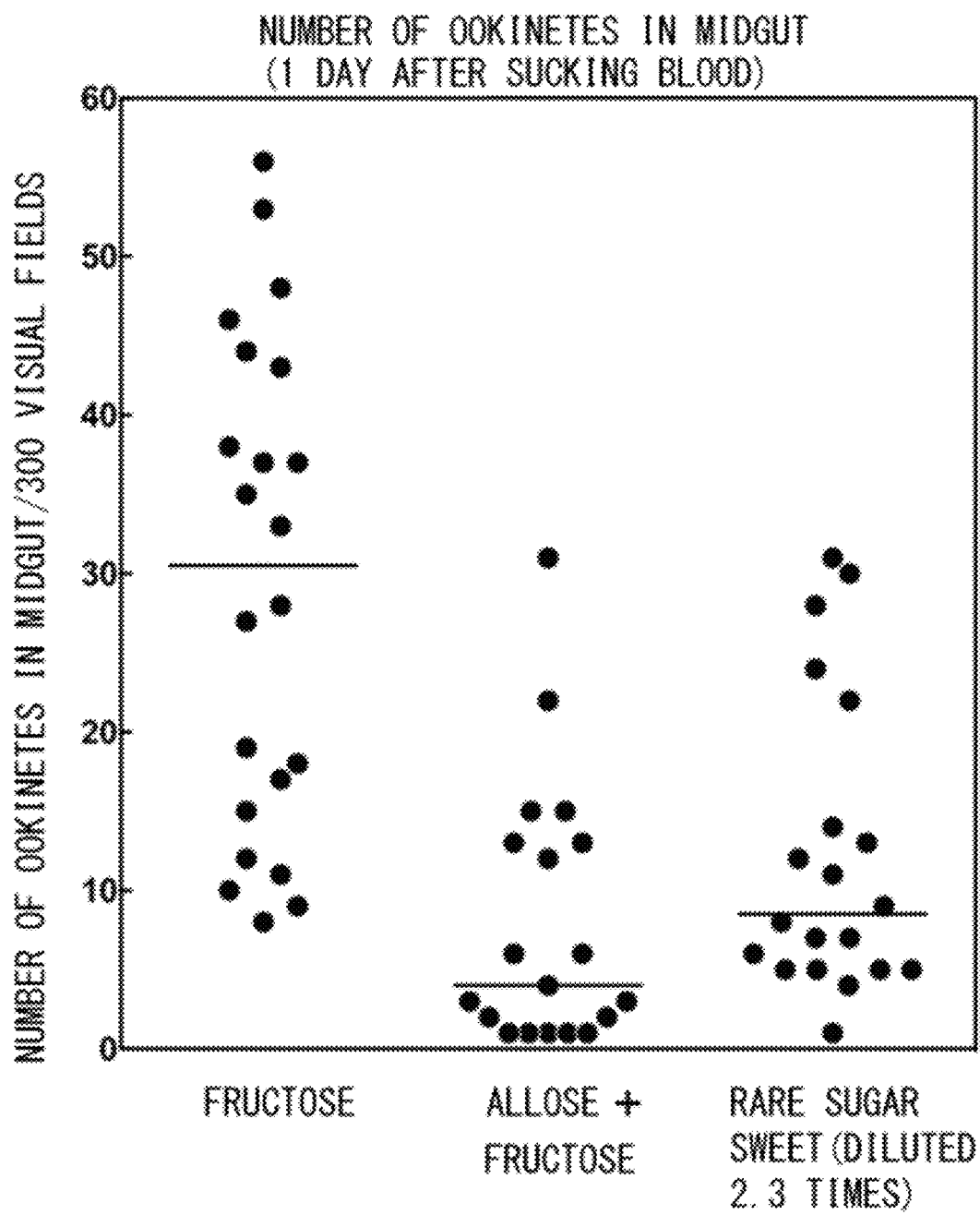

[fig.13]
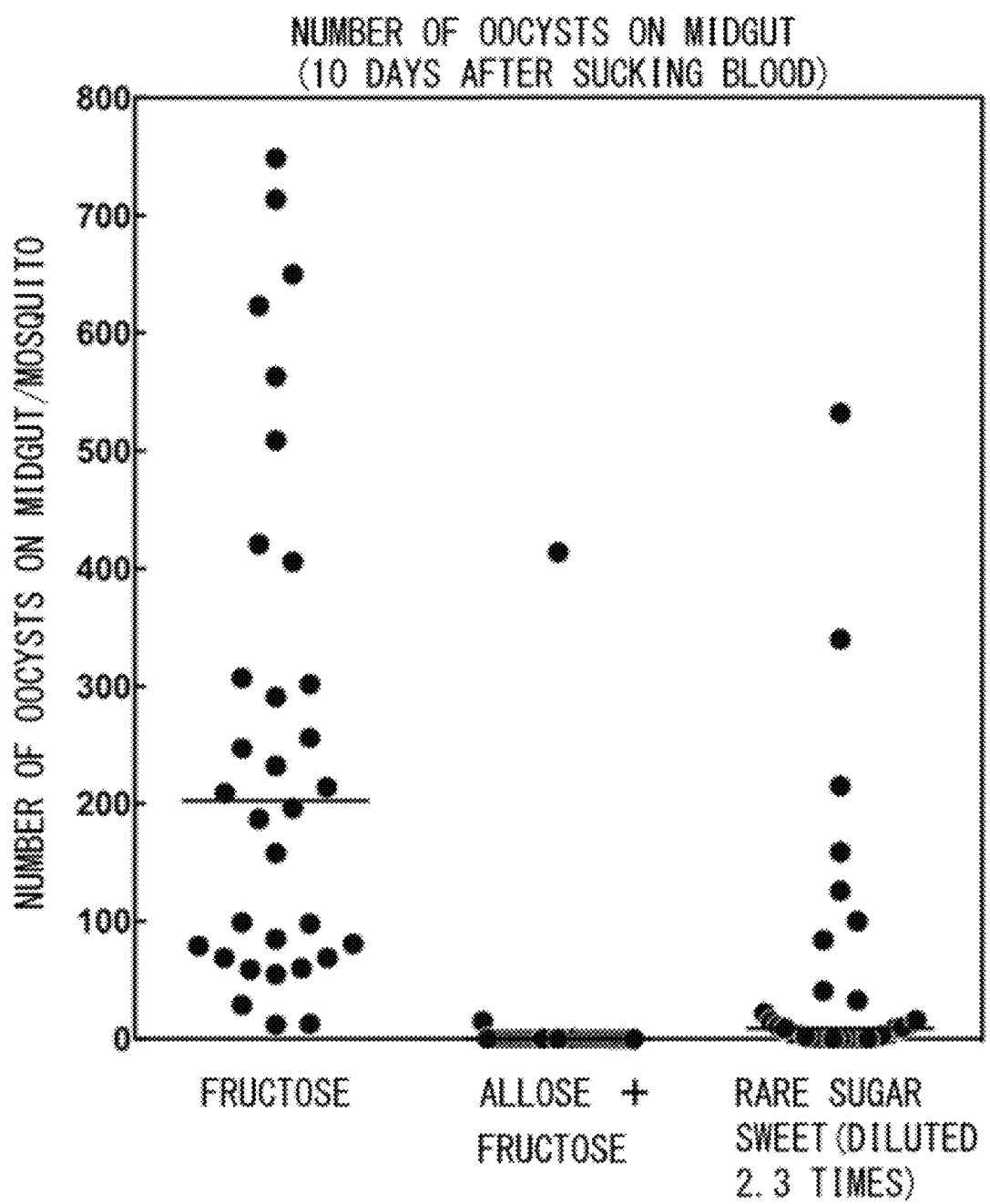

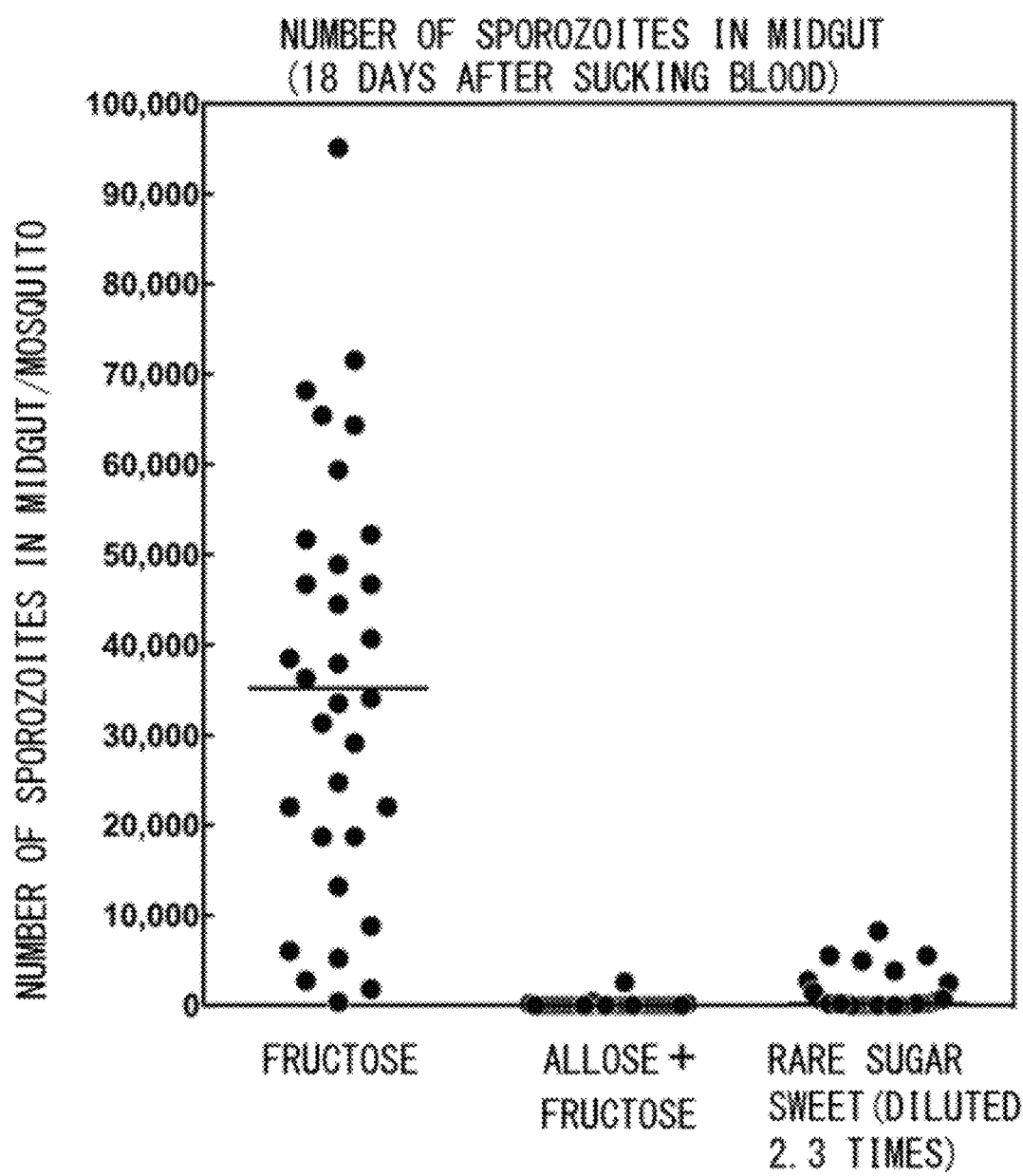
[fig.14]

[fig.15]
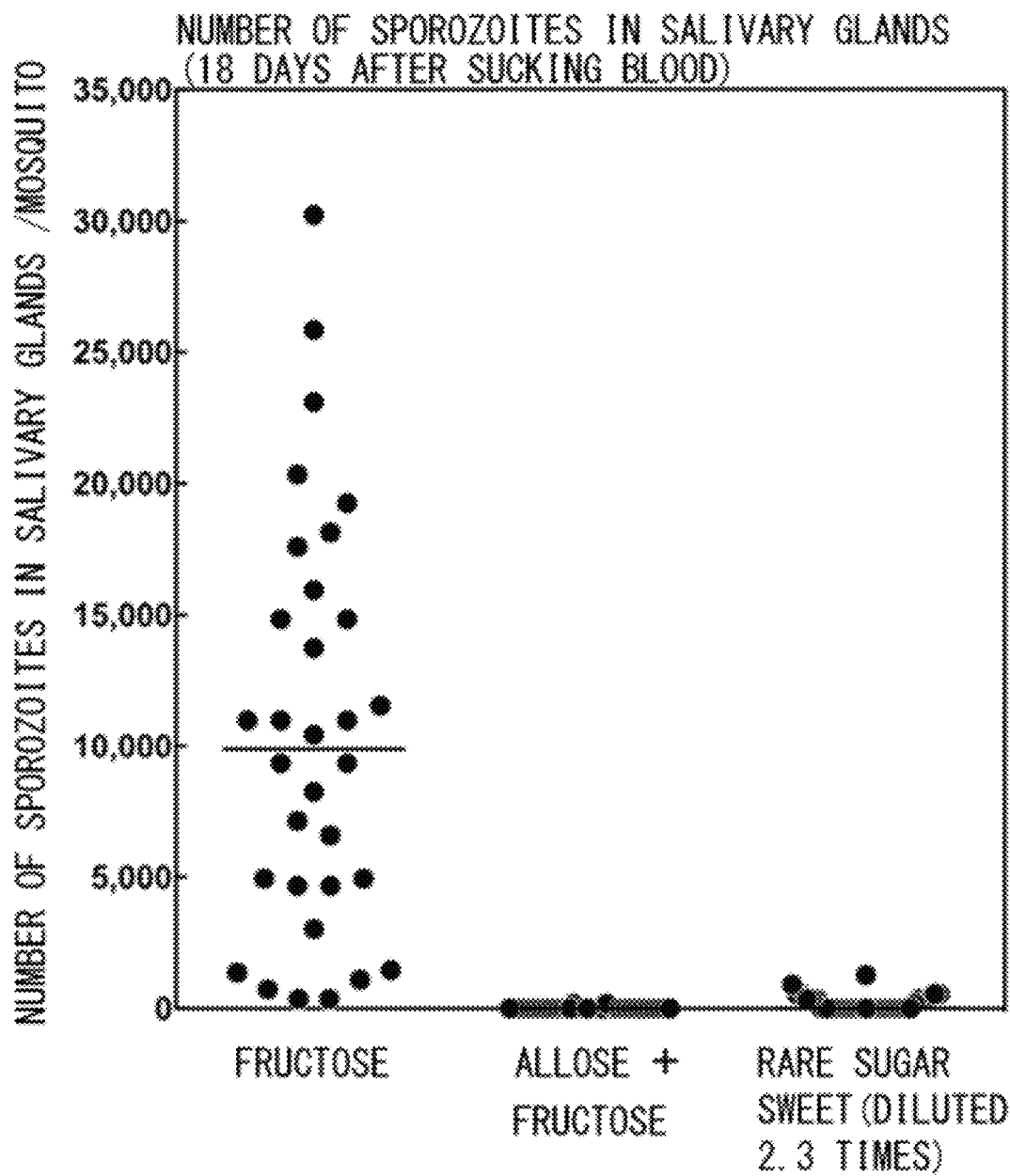

MALARIA TRANSMISSION PREVENTION AGENT HAVING RARE SUGAR AS EFFECTIVE COMPONENT THEREOF AND MALARIAL PARASITE GROWTH REGULATING AGENT

TECHNICAL FIELD

The present invention has been achieved based on the finding of the characteristics of a rare sugar as a drug for inhibiting malaria parasite development in a vector mosquito, and provides a malaria transmission blocker and a malaria parasite growth inhibitor, or a method for blocking malaria transmission, and a method for blocking malaria parasite development using these agents. The present invention can suppress the occurrence of patients with malaria, which is said to be a most significant protozoan parasitic infectious disease of humans, and causes about an estimated 200 million infected patients and about an estimated one million deaths per year.

BACKGROUND ART

Malaria is a mosquito-borne infectious disease and is still prevalent in a wide range of tropical and subtropical regions, causing 200 million or more clinical cases and 600,000 deaths (most of them are children under the age of five in sub-Saharan Africa) per year. About 40% of the world's population lives in regions where malaria is prevalent. Malaria is an infectious disease which is considered to be already eradicated in some advanced countries as well as tuberculosis and diphtheria. However, due to global warming, the region where malaria occurs is expanding also in a temperate region where malaria has rarely been confirmed so far, and there is a concern that malaria may be prevalent also in the main island of Japan in near future. This is considered to be because globalization has proceeded, migration of people has expanded globally, and the habitat of a vector mosquito has moved toward the north due to global warming. In addition, malaria parasites acquire resistance to various drugs, and therefore, spread of drug-resistant parasites and an increase in insecticide-resistant mosquitoes make the suppression of malaria difficult.

Under such circumstances, for the purpose of suppression of malaria, development of vaccines, elucidation of the biology and physiology of vector mosquitoes, elucidation of the physiological mechanism of malaria parasites, analysis of the immune response of humans, analysis of pathological conditions, development of novel antimalarial drugs, etc. have been studied from every angle. Above all, development of an effective vaccine has been demanded from the viewpoint of eradication of malaria.

At present, malaria is not prevalent in Japan, however, as the opportunity to go abroad increases as of late, cases where a person is infected abroad and develops the disease after returning to Japan are increasing. Malaria is caused by 4 types of parasites as pathogens, namely *Plasmodium vivax, Plasmodium falciparum, Plasmodium malariae*, and *Plasmodium ovale*. Recently, it is found that *Plamodium knowlesi* which is a monkey malaria agent, infects humans (zoonosis) and is called "fifth human malaria". The characteristic symptoms of malaria are chills, subsequent fever, and heavy sweating. The other signs of malaria are anemia, enlarged spleen, decreased blood flow in important organs, thrombocytopenia, acute renal failure, and so on. In addition, when a lesion extends to the central nervous system, delirium, convulsion, paralysis, and coma are developed, sometimes resulting in death when treatment is delayed. Clinically, *Plasmodium falciparum* malaria shows the highest pathogenicity, causing fulminant and/or cerebral malaria with high lethality.

Malaria is transmitted by a mosquito of the genus *Anopheles*. When a female mosquito takes a bloodmeal from a person infected with malaria, male and female gametocytes ingested into the mosquito gut, are activated and develop into gametes for subsequent fertilization. A zygote formed by fertilization differentiates into an ookinete which penetrates the midgut to form an oocyst under the midgut basement membrane. In about 2 weeks thereafter, thousands of sporozoites are formed in the oocyst. The formed sporozoites come out into the body cavity, and then gradually accumulate in the salivary gland. Then, when the mosquito sucks blood from a human again, the sporozoites invade the human body along with saliva. The sporozoites enter the bloodstream and travels to the liver, where they invade liver cells and differentiate into schizonts. Mature schizonts break the liver cells, releasing thousands of merozoites into the bloodstream, and each merozoite enters a red blood cells.

In the red blood cell, the merozoites grow into rings (ring forms or early stage trophozoites), then trophozoites (late-stage trophozoites), and thereafter into schizonts. Mature schizonts break the red blood cell membrane, releasing many merozoites into the bloodstream, and each merozoite invade a new red blood cell.

By repeating this cycle, the parasite proliferates. While repeating the asexual cycles, a small portion of the parasites differentiate into gametocytes, which perform the above-mentioned sexual reproduction when they are taken up by a mosquito, but will die sooner or later when they are not transferred into a mosquito.

As a therapeutic drug for the above-mentioned malaria, a drug which kills or suppresses the growth of rings, trophozoites, or the like in an intraerythrocytic growth stage has been used, and as such a drug, chloroquine, Fansidar, quinine, mefloquine, and the like are known. These drugs all have relatively high toxicity and have adverse effects such as gastrointestinal injuries, headache, and fever, and therefore, are not always satisfactory therapeutic drugs for malaria from the viewpoint of toxicity to humans and adverse effects. In addition, these drugs have a problem that parasites which are resistant to these drugs increase. An artemisinin-based drug which has begun to be used recently plays an important role as the last bastion of the therapeutic drug for malaria, and it is recommended that the drug should be always used in combination with another antimalarial drug in order to prevent the emergence of a resistant parasite. However, it has been reported that a parasite resistant to the artemisinin-based drug has already emerged in some regions. In addition, there are antigenic variations in vaccine target antigens for malaria parasites, and therefore, there is also a problem that it is difficult to develop vaccines. Because of these reasons, the current situation is that with respect to the treatment of malaria, the treatment strategy varies with country.

As the therapeutic drug for malaria, for example, the following literatures can be exemplified.

A therapeutic drug for malaria containing a compound having an acyl residue such as an ω3 fatty acid, for example, 5,8,11,14,17-eicosapentaenoic acid (EPA), 4,7,10,13,16,19-docosahexaenoic acid (DHA), or the like (specifically, a DHA ethyl ester or the like) as an active ingredient (PTL 1), a therapeutic drug for malaria composed of a novel compound including a D(+)-glucose derivative capable of efficiently delivering quinolone to a parasite (PTL 2), and an antimalarial drug composed of a tetrapyrrole derivative or a salt thereof such as biliverdin and having an action of inhibiting the invasion of merozoites in red blood cells and also suppressing the growth of developing bodies in red blood cells such as rings or trophozoites (PTL 3) have been proposed.

Further, also the following compounds have been proposed as a therapeutic drug for malaria.

For example, the use of riminophenazine in the production of a pharmaceutical product for treating parasitic infection is provided (PTL 4), a preventive or therapeutic drug for a parasite infectious disease which is a preventive or therapeutic drug for a parasite infectious disease containing an ω3 fatty acid and an antioxidant, and contains, for example, 5,8,11,14,17-eicosapentaenoic acid (EPA) or 4,7,10,13,16,19-docosahexaenoic acid (DHA), and vitamin E (PTL 5), and a drug for killing a malaria parasite containing kijimicin or a salt thereof as an active ingredient and a preventive and therapeutic drug for a malaria disease utilizing this (PTL 6).

CITATION LIST

Patent Literature

PTL 1: JP-A-5-148140
PTL 2: JP-A-2008-1630
PTL 3: JP-A-6-157308
PTL 4: JP-A-8-231401
PTL 5: JP-A-2004-307428
PTL 6: JP-A-2001-278787

Non Patent Literature

NPL 1: Journal of Applied Glycoscience, Vol. 5, No. 1 44-49 (2015)

SUMMARY OF INVENTION

Technical Problem

Even in the current situation that medical science has been developed, malaria has been rampant as one of the three major infectious diseases in the world. There are three specific methods for preventing or dealing with malaria, namely, a measure for prevention of mosquito bites, prophylactic treatment, and a treatment after developing the disease. The most basic prevention method in a malaria endemic region is a device for not being bitten by mosquitoes, that is, a measure for prevention of mosquito bites. This method is inexpensive, and has few side effect of a drug on the human body, and moreover, the preventive effect is high when the measure is performed thoroughly. The measure for prevention of mosquito bites in a malaria endemic region should be performed by all the residents, however, in fact, residential facilities are inadequate, going out in a time zone after evening cannot be avoided, etc., and therefore, it is difficult to completely perforin the measure for prevention of mosquito bites in a wide region.

As for a method using a drug, there are two methods: prophylactic treatment (to take an antimalarial drug for the purpose of prevention) and a treatment after developing the disease. However, in both methods, the problem of adverse effects of the drug cannot be ignored.

In studies for suppressing malaria having been conducted so far, efforts have been made in the following field for solving the conventional problems.

1. Development of novel diagnostic method: In a diagnosis, microscopy is simple and accurate and is widely used even at present, however, a genetic diagnosis such as PCR is performed only in developed countries. Further, a rapid diagnosis kit by immunochromatography is useful, but is not in common use at present. Under such circumstances, development of a diagnostic method which does not require blood collection has been demanded.

2. Development of novel antimalarial drug: Also from the viewpoint that the emergence of a parasite resistant to an artemisinin-foased drug which is becoming the mainstream at present has already been reported, development of a drug for which drug resistance is less likely to occur has been demanded, however, pharmaceutical companies are unwilling to perform research and development therefor.

3. Development of malaria vaccine: Even if an effect can be confirmed in a laboratory level, the hurdle for clinical studies is high, and pharmaceutical companies are unwilling to perform research and development therefor.

4. Measure for vector mosquito: As for spraying of an insecticide, it is difficult to spray a large amount of an insecticide from the viewpoint of the impact on the environment and cost, and also the emergence and spread of mosquitoes resistant, to the insecticide cannot be avoided. The use of a mosquito net impregnated with an insecticide is a highly effective measure, however, it is not sufficiently popularized.

In consideration of the current situation and problems of the medical field related to prevention and treatment of malaria as described above, the present inventors aimed to find a drug (compound) which inhibits malaria parasite growth in the body of a mosquito by allowing a vector mosquito to take the drug (compound) as a novel method for a measure for a vector mosquito and made intensive efforts for setting the goal to develop currently available drugs (compounds) as reprofiling for search for the drug (compound) from the viewpoint of safety, and thus, achieved the present invention.

That is, the present invention provides a malaria parasite growth inhibitor containing a rare sugar as an active ingredient, and particularly provides a malaria transmission blocker capable of inhibiting parasite growth in the body of a vector mosquito by allowing a malaria vector mosquito to take a rare sugar.

The conventional prevention or treatment of malaria using a drug intends to kill a malaria parasite by administering a drug to the human body, and therefore, a risk for development of adverse effects cannot be avoided, however, the malaria parasite growth inhibitor of the present invention can avoid the concern for adverse effects on the human body and safety. Since D-allose and D-psicose used in the present invention are substances also used as a sweetener, for example, even if children accidentally ingest the malaria parasite growth inhibitor of the present invention, there are not any toxic effects.

Solution to Problem

The gist of the present invention is a malaria parasite growth inhibitor described in the following (1) to (4).

(1) A malaria parasite growth inhibitor, characterized by containing a rare sugar as an active ingredient.

(2) The malaria parasite growth inhibitor according to the above (1), wherein the rare sugar is D-allose or D-psicose.

(3) The malaria parasite growth inhibitor according to the above (1) or (2), which inhibits a malaria parasite from growing in the body of a vector mosquito.

(4) The malaria parasite growth inhibitor according to the above (3), which inhibits a stage in which a malaria parasite grows into any of an ookinete, an oocyst, and a sporozoite in the body of a vector mosquito.

Further, the gist of the present invention is a method for inhibiting malaria parasite growth in the body of a mosquito described in the following (5) to (8).

(5) A method for inhibiting malaria parasite growth in the body of a mosquito, characterized by feeding a vector mosquito with a rare sugar.

(6) The method for inhibiting malaria parasite growth in the body of a mosquito according to the above (5), wherein the vector mosquito is fed with a solution of a rare sugar at a concentration of 10 mM to 100 mM.

(7) The method for inhibiting malaria parasite growth in the body of a mosquito according to the above (5) or (6), wherein the rare sugar is D-allose or D-psicose.

(8) The method for inhibiting malaria parasite growth in the body of a mosquito according to any one of the above (5) to (7), wherein a stage in which a malaria parasite grows into any of an ookinete, an oocyst, and a sporozoite in the body of a mosquito is inhibited.

Further, the gist of the present invention is a malaria parasite transmission blocker described in the following (9) to (12).

(9) A malaria parasite transmission blocker, characterized by containing a rare sugar as an active ingredient.

(10) The malaria parasite transmission blocker according to claim 9, which is fed to a vector mosquito.

(11) The malaria parasite transmission blocker according to the above (9) or (10), wherein the rare sugar is contained at a concentration of 10 mM to 100 mM.

(12) The malaria parasite transmission blocker according to any one of the above (9) to (11), wherein the rare sugar is D-allose or D-psicose.

Advantageous Effects of Invention

According to the present invention, the following advantageous effects are obtained.

1. The malaria parasite growth in the body of a vector mosquito is inhibited, and a sporozoite is not formed. Due to this, even if a person is bitten by a vector mosquito, the person is not infected with malaria.

2. The use of the malaria parasite transmission blocker or the malaria parasite growth inhibitor is simple.

3. The rare sugar serving as the active ingredient is a sugar which exists in nature and is used as a sweetener or the like at present, and therefore, has an extremely low side effect on the human body or nature.

4. Since the drugs do not disrupt the natural environment unlike insecticides, the drugs can be applied continuously to a vector mosquito over a long period of time in a wide range of regions.

5. It is possible to easily achieve the practical use for developing currently available compounds as reprofiling.

6. Since the rare sugar is a compound, which exists in nature, the possibility of the emergence of a malaria parasite resistant to the rare sugar is low.

BRIEF DESCRIPTION OF DRAWINGS

FIG. 1 shows the life history of a malaria parasite in the human body.

FIG. 2 shows the life history of a malaria parasite in the body of a vector mosquito.

FIG. 3 shows an experimental method for examining a malaria transmission blocking effect of a rare sugar.

FIG. 4 shows the number of ookinetes in the midgut of a vector mosquito when one day passed after sucking blood in Example 1.

FIG. 5 shows the number of oocysts on the midgut of a vector mosquito when 10 days passed after sucking blood in Example 1.

FIG. 6 shows the number of sporozoites in the midgut of a vector mosquito when 18 days passed after sucking blood in Example 1.

FIG. 7 shows the number of sporozoites in the salivary glands of a vector mosquito when 18 days passed after sucking blood in Example 1.

FIG. 8 shows the number of ookinetes in the midgut of a vector mosquito when one day passed after sucking blood at a D-allose concentration of 0 to 100 mM in Example 3.

FIG. 9 shows the number of oocysts on the midgut of a vector mosquito when 10 days passed after sucking blood at a D-allose concentration of 0 to 100 mM in Example 3.

FIG. 10 shows the number of sporozoites in the midgut of a vector mosquito when 18 days passed after sucking blood at a D-allose concentration of 0 to 100 mM in Example 3.

FIG. 11 shows the number of sporozoites in the salivary glands of a vector mosquito when 18 days passed after sucking blood at a D-allose concentration of 0 to 100 mM in Example 3.

FIG. 12 shows the number of ookinetes in the midgut of a vector mosquito when one day passed after sucking blood in Example 5.

FIG. 13 shows the number of oocysts on the midgut of a vector mosquito when 10 days passed after sucking blood in Example 5.

FIG. 14 shows the number of sporozoites in the midgut of a vector mosquito when 18 days passed after sucking blood in Example 5.

FIG. 15 shows the number of sporozoites in the salivary glands of a vector mosquito when 18 days passed after sucking blood in Example 5.

DESCRIPTION OF EMBODIMENTS

Conventionally, great importance has been placed on disappearance of the symptoms of malaria by administering a drug so as to exterminate a malaria parasite invading the human body or inhibit the growth thereof. However, the present invention enables the condition that "even if blood is sucked by an infected mosquito, a person does not develop malaria" by inhibiting malaria parasite growth in the body of a malaria vector mosquito.

That is, in the present invention, even if a person is bitten by a vector mosquito, the person is not infected with malaria by inhibiting a malaria parasite from growing in the body of the vector mosquito so that sporozoites are not formed, which is achieved by feeding a vector mosquito with a rare sugar as a malaria parasite growth inhibitor.

Malaria is roughly divided into *Plasmodium falciparum* malaria, *Plasmodium vivax* malaria, *Plasmodium ovale* malaria, and *Plasmodium malariae* malaria, and the characteristics thereof are shown in the following table 1, however, in particular, *Plasmodium falciparum* malaria causes a severe complication, and a drug-resistant parasite emerges, which have become serious problems.

TABLE 1

Types and Characteristics of Malaria

| Type | Latent period* | Fever pattern | Complication | Geographical distribution | Drug resistance |
|---|---|---|---|---|---|
| *Plasmodium falciparum* malaria | 7 to 21 days, or more | Every day, sometimes a plurality of times per day | Encephalopathy, pulmonary edema/ ARDS, acute renal failure, DIC-like bleeding tendency, profound anemia, metabolic acidosis, hypoglycemia, hepatic disorder | sub-Saharan Africa, South Asia, Indochina peninsula, Indonesia, Philippine, southern part of China, Melanesia, Amazon river basin in South America | Seriously problematic |
| *Plasmodium vivax* malaria | 12 to 17 days, or more | Every day in the beginning, and later every other days | no particular complication | North Africa, Middle East, throughout Asia Melanesia, Latin America | Problematic to some extent |
| *Plasmodium ovale* malaria | 16 to 18 days, or more. | Every day in the beginning, and later every other days | no particular complication | sub-Saharan Africa | Hardly problematic |
| *Plasmodium malariae* malaria | 18 to 40 days, or more. | Every day in the beginning, and later every three days | nephrotic syndrome that becomes chronic | Distributed sporadically in countries around the world | Unknown |

*In the case where malaria is developed when preventive internal administration has been performed, the latent period may be as long as 2 to 3 months.

[Life History of Malaria Parasite in Human Body]

The life history of a malaria parasite in the human body is shown in FIG. 1.

When a mosquito infected with malaria parasites sucks blood, sporozoif.es are injected into the human body. The sporozoite invades a liver cell through the bloodstream in several tens of seconds to several minutes. A malaria parasite performs asexual reproduction in the liver cell to produce several thousands of merozoites. This growth stage is called exoerythrocytic growth, and the parasite form is called an exoerythrocytic parasite. The merozoites rupture the liver cell to emerge, and recognize a specif ic receptor on a red blood cell and penetrate into the red blood cell. The merozoite invading the red blood cell grows into a ring-shaped form, an ameba-like trophozoite, an immature schizont, and a mature schizont, and then, many merozoites are formed again. When the schizont. matures, the red blood cell bursts, and the merozoites are released in blood. The merozoite invades a new red blood cell in a short time, and the same cycle is repeated. In this manner, the merozoite penetrating into a red blood cell grows into an erythrocytic parasite and aggressively proliferates. The symptoms in the human body in this acute stage are severe chills and high fever accompanying rupture of red blood cells, and periodic fever is repeated in malaria other than *Plasmodium falciparum* malaria. When rupture of red blood cells proceeds, anemia and enlarged spleen are caused in the patient, however, in the case of *Plasmodium falciparum* malaria, a lethal complication such as encephalopathy or renal failure may be further caused in some cases. This process is called an intraerythrocytic cycle. During intraerythrocytic cycles, some portion of parasites differentiate into gametocytes. In the gametocytes, there are male gametocytes and female gametocytes, and after migration into a vector mosquito, they perform sexual reproduction.

[Life History of Malaria Parasite in Body of Vector Mosquito]

The life history of a malaria parasite in the body of a vector mosquito is shown in FIG. 2.

Among the male and female gametocytes incorporated in the body of a vector mosquito along with human blood, the male gametocyte produces male gametes in the midgut of the vector mosquito (release of a flagellum), and the female gametocyte develops into a female gamete, and both gametes fuse and fertilize to form a zygote. The zygote differentiates into an ookinete having motility, and the ookinete penetrates the midgut wall and migrates to the outside thereof to form an oocyst. The oocyst grows over about 2 weeks, and thousands of sporozoites are formed therein. Before long, the oocyst bursts and the sporozoites are released into the body cavity. Thereafter, the sporozoites migrate to the salivary gland, and when the mosquito sucks blood of a human again, the sporozoites are injected into the human body.

The gametocyte incorporated in the body of a vector mosquito develops into an ookinete about 2 4 hours after fertilization, and after about 2 to 3 days, the ookinete penetrates the midgut, and after about 5 days, an oocyst is formed on the midgut wall. After about 10 days, sporozoites are formed in the oocyst, and the oocyst bursts before long. After about 15 days, the sporozoites are accumulated in the salivary glands.

[Intake of Rare Sugar by Vector Mosquito]

An anopheline mosquito which mediates malaria lives in water during a larva stage, and thereafter develops into a pupa, and then develops into an adult from the pupa. The adult mosquito takes fruit juice as a feed and can live for a relatively long period with a saccharide contained in the fruit juice. Among anopheline mosquitoes, only female mosquitoes suck blood. This is because it is necessary to obtain enough nutrients from bloodmeal for subsequent egg production.

In the present invention, in order to feed a vector mosquito with a rare sugar, for example, it is easy to give an aqueous solution of a rare sugar. A vector mosquito can take a saccharide as a feed, and therefore, it is possible to perform feeding in the form of a mixed solution of a saccharide such as fructose or glucose with a rare sugar. A time when a vector mosquito is fed with a rare sugar is not particularly limited, and it is preferred that a rare sugar always exists in the body of the vector mosquito. In order to feed a rare sugar, it is preferred that a rare sugar solution is placed in a container, a portion of a material which absorbs water such as a filter paper is dipped in the solution, and a vector mosquito is made to be able to easily take the rare sugar solution from the material having sucked the rare sugar.

In order to feed a vector mosquito with a rare sugar so as to exhibit the operation and effect of the present invention, it is necessary to set the concentration of the rare sugar solution in a range of 10 mM to 500 mM, preferably in a range of 30 mM to 300 mM, more preferably in a range of 50 mM to 200 mM.

In order to exhibit the malaria parasite growth inhibitory effect of a rare sugar, it is necessary to set the concentration to 10 mM or more, however, as the concentration increases from this concentration, the inhibitory effect increases. However, it is not appropriate to set the concentration to 500 mM or more from the viewpoint of economic efficiency or a correlation between the concentration and the inhibitory effect.

In order to block malaria transmission by decreasing the number of sporozoites in the salivary glands of a mosquito to 0, it is preferred to set the concentration of a rare sugar to 75 mM or more.

In order to allow a vector mosquito to take an aqueous rare sugar solution, it is preferred to perform feeding by mixing a saccharide such as fructose, glucose, or sucrose to serve as a feed for the vector mosquito, and the concentration of such a saccharide is not particularly limited, but is preferably set within a concentration range preferred by the mosquito.

[Rare Sugar]

The rare sugar used as the malaria parasite growth inhibitor of the present invention is not necessarily a pure substance obtained by purification, and may contain various types of rare sugars and other saccharides.

The rare sugar in the present invention is defined as monosaccharides (aldoses and ketoses) and derivatives thereof (sugar alcohols) which exist only in a small amount in nature with respect to "naturally occurring monosaccharides" typified by D-glucose which exits in a large amount in nature among monosaccharides (there are 34 types of monosaccharides having 6 carbon atoms (hexoses) in total, in which there are 16 types of aldoses, 8 types of ketoses, ana 10 types of sugar alcohols), each of which is a basic unit of a sugar. In general, as the aldose which exists in a large amount in nature, there are 6 types: D-glucose, D-galactose, D-mannose, D-ribose, D-xylose, and L-arabinose, and the other aldoses are defined as rare sugars. As the ketose, there exists D-fructose, and the other ketoses can be defined as rare sugars. Examples of the other ketoses include D-psicose, D-tagatose, D-sorbose, L-fructose, L-psicose, L-tagatose, and L-sorbose. Further, the sugar alcohol can be formed by reducing a monosaccharide, however, in nature, D-sorbitol exists in a relatively large amount, and the other sugar alcohols exist in a small amount in nature, and therefore can be defined as rare sugars. The existing amount of the rare sugar is very small, and for example, the existing amount of D-allose is overwhelmingly small as compared with that of D-glucose.

Among these, at present, the rare sugars which can be produced in a large amount are D-psicose and D-allose. D-psicose is the D form of psicose classified as a ketohexose and is a hexose. Further, D-allose is the D form of allose classified as an allose and is also a hexose. D-psicose may be obtained by any method including one extracted from nature, one synthesized by a chemical or biological method, and the like. D-allose can be obtained by allowing D-xylose isomerase to act on a solution containing D-psicose to produce D-allose from D-psicose, or the like, however, the method is not limited thereto, and D-psicose may be obtained by any method.

Among the above-mentioned rare sugars, for example, as a method for obtaining D-allose, a method of synthesizing it from D-psicose using L-rhamnose isomerase, a method of obtaining it by allowing D-xylose isomerase to act on a solution containing D-psicose, and the like are disclosed, however, D-allose in the present invention is not limited thereto, and D-allose may be one obtained by any method, for example, one obtained by isomerization through a chemical treatment method or the like. Further, as a method for obtaining D-psicose, a production method capable of obtaining D-psicose by treating fructose with an enzyme (epimerase) is generally used at present, however, the method is not limited thereto, and D-psicose may be one obtained by a production method utilizing a microorganism which produces the enzyme, one extracted from a natural substance, or one contained in a natural substance which may be used as it is, or one obtained by isomerization through a chemical treatment method. In addition, a method for purifying D-psicose utilizing an enzyme is known.

As the rare sugar in the present invention, any of the above-mentioned rare sugars (for example, D-sorbose, D-tagatose, L-sorbose, D-psicose, D-allose, and D-altrose) can be appropriately selected and used. In particular, the rare sugar can be used in the form of a rare sugar-containing syrup. The rare sugar-containing syrup can be obtained by appropriately selecting any of the above-mentioned rare sugars (for example, D-sorbose, D-tagatose, L-sorbose, D-psicose, D-allose, and D-altcrose) and appropriately mixing the selected sugar with a common syrup (liquid sugar), but can be easily obtained as a commercially available product "Rare Sugar Sweet" (distributor: Rare Sweet Co., Ltd., seller: Matsutani Chemical Industry Co., Ltd.). The "Rare Sugar Sweet" is a syrup containing rare sugars obtained using an isomerized sugar as a raw material, and is produced so as to mainly contain D-psicose and D-allose as the rare sugars. As the rare sugars contained in the rare sugar-containing syrup obtained by the method, D-psicose is contained in an amount of 0.5 to 17 mass % and D-allose is contained in an amount of 0.2 to 10 mass % with respect to the total sugars, however, rare sugars which have not been identified yet are also contained. D-allose and psicose may be separated and purified from this syrup and used, however, the use of the syrup as it is, is also contemplated.

The method for obtaining the rare sugar-containing syrup is not limited to the above method, and a syrup containing various types of monosaccharides (including rare sugars) generated by allowing an alkali to act on a monosaccharide (D-glucose or D-fructose), and causing a Lobry de Bruyn and Alberda van Ekenstein rearrangement reaction, which is a reaction discovered in the late $19^{th}$ century, or a retroaldol reaction and the subsequent aldol reaction (the above reactions are referred to as alkali isomerization reaction) can be widely referred to as "rare sugar-containing syrup", and a syrup obtained by alkali isomerization using D-glucose and/or D-fructose as a raw material until the content of D-glucose and/or D-fructose falls within a range of 55 to 99 mass %. NPL: 1 reports that with respect to the above-mentioned commercially available product "Rare Sugar Sweet", in the syrup containing the rare sugars, D-psicose (5.4 g/100 g), D-sorbose (5.3 g/100 g), D-tagatose (2.0 g/100 g), D-allose (1.4 g/100 g), and D-mannose (4.3 g/100 g) were contained.

[Examination of Malaria Transmission-Blocking Effect]

The present invention blocks the formation of sporozoites in the body of a mosquito by inhibiting malaria parasite development in a vector mosquito, and therefore, even if a person is bitten by a mosquito, a malaria parasite does not invade the human body, whereby malaria transmission is blocked.

In order to block malaria transmission, a vector mosquito is fed with a feed containing a rare sugar in advance, and then made to suck blood of a mouse infected with *Plasmodium berghei* parasite, whereby garaetocytes are ingested into the midgut of the vector mosquito. Thereafter, the feed containing a rare sugar is continuously given to the mosquito, and at the time point when one day has passed after the gametocytes are ingested into the body, the number of ookinetes in the midgut is evaluated, and then, the number of oocysts on the midgut after 10 days, the number of sporozoites in the midgut and the number of sporozoites in the salivary glands after 18 days are evaluated. In this manner, the malaria parasite growth inhibitory effect of the rare sugar was examined.

As a result, the formation of ookinetes in the midgut after one day was suppressed to some extent by D-psicose, however, it was not suppressed by D-allose. The formation of oocysts on the midgut after 10 days was suppressed by D-allose. Further, the formation of sporozoites in the midgut and in the salivary glands after 18 days were suppressed by D-allose. From these results, it was found that the feeding of the rare sugar affects the malaria parasite growth by using D-allose or D-psicose, both of which are rare sugars.

20 days after sucking blood of an infected mouse, each group of mosquitoes which had been fed with a rare sugar (D-allose or D-psicose) and a control group of mosquitoes which had not been fed with a rare sugar were made to suck blood of mice, and the infectivity of malaria in mice was examined. As a result, in a group in which the mosquitoes fed with D-allose were made to suck blood, malaria infection was not observed in about 70% of mice, and the infection inhibitory effect of a rare sugar was confirmed.

Next, the present invention will be specifically described based on Examples. In Examples 1 to 4, an *Anopheles stephensi* mosquitoes fed with a sugar liquid containing a rare sugar D-allose were made to suck blood of a mouse infected with *Plasmodium berghei* parasite, and thereafter continuously fed with the D-allose-containing sugar liquid successively, and if was revealed that malaria parasite growth in the body of the mosquito was inhibited. Further, in Examples 5 and 6, the same experiment was performed using Rare Sugar Sweet (containing D-allose) which is a commercially available rare sugar-containing sugar liquid, and as a result, it was revealed that Rare Sugar Sweet diluted 2.3 times has a transmission-blocking effect.

These results show a possibility that in addition to the D-allose-containing sugar liquid prepared individually, also the commercially available D-allose-containing rare sugar liquid can be applied as a malaria transmission blocker in an endemic region.

Incidentally, the present invention is not limited to these Examples.

Example 1

A malaria parasite growth blocking effect of a rare sugar was examined. FIG. 3 schematically shows an experimental method for examining a malaria transmisson-blocking effect of a rare sugar.

First, three groups, each of which includes about 200 *Anopheles stephensi* mosquitoes, were prepared, and in a first group, a mixed aqueous solution of 100 mM D-allose and 440 mM D-fructose was fed, in a second group, a mixed aqueous solution of 100 mM B-psicose and 440 mM D-fructose was fed, and in a third group, an aqueous solution of 440 mM D-fructose was fed, which was used as a control. Each of these aqueous solutions was placed in an Erlenmeyer flask, and a lower end portion of a filter paper was dipped in the aqueous solution, and *Anopheles stephensi* mosquitoes were fed with the aqueous solution absorbed in the filter paper.

Further, red blood cells infected with *Plasmodium berghei* parasite were intraperitoneally administered to BALB/c mice (6 weeks of age, female), whereby mice infected with malaria were prepared.

*Anopheles stephensi* mosquitoes in each group were made to suck each aqueous solution for 3 days, and thereafter, made to suck blood of the mice infected with *Plasmodium berghei* malaria, whereby the malaria parasites were incorporated in the body of *Anopheles stephensi* mosquitoes. Subsequently, while continuously giving the fructose aqueous solution containing a rare sugar or the aqueous solution containing only fructose, the number of parasites in the body of the mosquitoes was evaluated at the below-mentioned timings. That is, 24 hours after sucking infected blood, the number of ookinetes in the midgut was counted, the number of oocysts on the midgut was counted after 10 days, and the number of sporozoites in the midgut and in the salivary glands were counted after 18 days, and the results of the three groups were compared. The results are shown in FIGS. 4 to 7.

FIG. 4 shows the results of counting the number of ookinetes in the midgut of the mosquito when one day passed after sucking blood. The formation of ookinetes was somewhat suppressed by D-psicose, however, the suppression by D-allose was slight. 10 days after sucking blood, that is, as a result of counting the number of oocysts formed by ookinetes penetrating the midgut, the number of oocysts in the D-allose feeding group was suppressed by 95% as compared with the control group, however, in the D-psicose feeding group, the formation of oocysts was slightly promoted (FIG. 5). The number of sporozoites in the midgut 18 days after sucking blood was suppressed by 98.7% in the D-allose feeding group as compared with the control group, and suppressed by about 60% in the D-psicose feeding group. On the other hand, the number of sporozoites in the salivary gland after 18 days, the same as above, was suppressed by 98.5% in the D-allose feeding group, however, in the D-psicose feeding group, the formation of sporozoites slightly exceeding that in the control was observed.

Example 2

Each of the *Anopheles stephensi* mosquitoes in the three groups fed with the feed for 20 days in the above Example 1 was made to suck blood of the BALB/c mice (6 weeks of age, female). In each group, 50 mosquitoes were made to suck blood of 5 mice for 1 minute 5 times for each mouse. Every day from 2 days after sucking blood, a smear preparation was prepared from a small amount of blood collected from the tail of each mouse, followed by Giemsa staining, and thereafter, the presence or absence of parasites was examined with a microscope. In some mice, parasites were confirmed 3 days after sucking blood, and thereafter, the incidence rate increased, however, whether or not malaria was developed was determined based on the presence or absence of parasites at the time point of 14 days after sucking blood in the end.

The results are shown in Table 2. In the D-psicose feeding group and the control, the incidence rate was 100%, however, in the D-allose feeding group, the incidence rate was 29%. This shows that the malaria transmission ability of Anopheles stephensi mosquitoes fed with D-allose was significantly suppressed.

TABLE 2

Infectivity to Mice

| | Incidence rate after sucking blood (%) (mice which developed malaria/mice which had their blood sucked) |
|---|---|
| Fructose 440 mM | 100 (6/6) |
| Allose 100 mM + Fructose 440 mM | 29 (2/7) |
| Psicose 100 mM + Fructose 440 mM | 100 (6/6) |

In the mosquitoes fed with D-allose + D-fructose, malaria transmission was significantly suppressed.

Example 3

The D-allose concentration dependence for malaria parasite growth blocking effect of a rare sugar was examined. Four groups of Anopheles stephensi mosquitoes were prepared, and in a first group to a third group, mixed aqueous solutions of 10 mM, 30 mM, or 100 mM D-allose and 440 mM D-fructose were fed, respectively, and in a fourth group, an aqueous solution of 440 mM D-fructose was fed. In each of these aqueous solutions, a lower end portion of a filter paper was dipped, and Anopheles stephensi mosquitoes were fed with the aqueous solution absorbed in the filter paper.

Further, red blood cells infected with *Plasmodium berghei* parasite were intraperitoneally administered to BALB/c mice (6 weeks of age, female), whereby mice infected with malaria were prepared.

*Anopheles stephensi* mosquitoes in each group were made to suck each aqueous solution for 3 days, and thereafter, made to suck blood of the mice infected with *Plasmodium berghei* malaria, whereby the malaria parasites were incorporated in the body of *Anopheles stephensi* mosquitoes. Thereafter, while continuously giving the aqueous solution containing a rare sugar or the aqueous solution containing only fructose, the number of parasites in the body of the mosquitoes was counted at respective timings. That is, 24 hours after sucking infected blood, the number of ookinetes in the midgut, was counted, the number of oocysts on the midgut was counted after 10 days, and the number of sporozoites in the midgut and in the salivary glands were counted after 18 days, and the results of the four groups were compared. The results are shown in FIGS. 8 to 11.

FIG. 8 shows the results of counting the number of ookinetes in the midgut of the mosquito when one day passed after sucking blood. The growth into ookinetes was suppressed in a concentration-dependent manner in a D-allose concentration range from 10 mM to 100 mM. 10 days after sucking blood, that is, the number of oocysts formed by ookinetes penetrating the midgut was also suppressed in a D-allose concentration-dependent manner, and in particular, the growth of oocysts on the midgut was almost completely suppressed at 100 mM (FIG. 9). Further, also with respect to the number of sporozoites in the midgut and the number of sporozoites in the salivary glands 18 days after sucking blood, the same tendency was shown, and it was found that the formation of sporozoites is completely suppressed by feeding D-allose at 100 mM (FIGS. 10 and 11).

From these experimental results, it was demonstrated that malaria parasite differentiation growth in the body of a mosquito was suppressed in a D-allose concentration range from 10 mM to 100 mM.

Example 4

Each of the *Anopheles stephensi* mosquitoes in the four groups fed with the feed for 20 days in the above Example 3 was made to suck blood of the BALE/c mice (6 weeks of age, female). In each group, 50 mosquitoes were made to suck blood of 5 mice for 1 minute 5 times for each mouse. Every day from 2 days after sucking blood, a smear preparation was prepared from a small amount of blood collected from the tail of each mouse, followed by Giemsa staining, and thereafter, the presence or absence of parasites was examined with a microscope. Whether or not malaria was developed was determined at the time point of 14 days after sucking blood. The results are shown in Table 3. All the mice which had their blood sucked by the mosquitoes in the 10 mM D-allose feeding group, the 30 mM D-allose feeding group, and the fructose single feeding group developed malaria at 100%, however, all the mice which had their blood sucked by the mosquitoes in the 100 mM D-allose feeding group did not develop malaria. Also in the 30 mM D-allose feeding group, the incidence rate was 100%, however, malaria was developed one day later as compared with the 10 mM D-ailose feeding group and the fructose single feeding group. The onset of malaria one day later in the 30 mM D-allose feeding group suggests that the number of sporozoites inoculated into the mice when having their blood sucked was about one-tenth, which matches the results that the number of sporozoites in the salivary glands significantly decreased in this group, and also shows that it is difficult to decrease the ratio of malaria transmission by sucking blood to 0 as long as sporozoites remain in the salivary glands even if the number of sporozoites is small. In this experiment, it is shown that the malaria transmission ability of *Anopheles stephensi* mosquitoes fed with D-allose was significantly suppressed, and in particular, the incidence rate was suppressed by 100% in the mice which had their blood sucked by the mosquitoes in the 100 mM D-allose feeding group, which is worthy of mention.

TABLE 3

Infectivity to Mice

| | Incidence rate after sucking blood (%) (mice which developed malaria/mice which had their blood sucked) | |
|---|---|---|
| Fructose 440 mM | 100 (5/5) | |
| Allose 10 mM + Fructose 440 mM | 100 (5/5) | |
| Allose 30 mM + Fructose 440 mM | 100 (5/5) | The onset was delayed one day as compared with the mice in the above groups. |
| Allose 100 mM + Fructose 440 mM | 0 (0/5) | |

In the mosquitoes fed with 100 mM D-allose + D-fructose, malaria transmission was completely inhibited. (amazing!)

Example 5

In Examples 1 and 2, it was shown that 100 mM D-allose (+440 mM D-fructose) completely blocks malaria transmission, however, in Example 5, a malaria transmission-blocking effect of Rare Sugar Sweet (RSS) which has already been sold in common stores was verified.

RSS is a liquid sugar having a sugar content of 70%, and it was difficult to make mosquitoes suck the stock solution as it is, and therefore, RSS was diluted 2.3 times so that the sugar content was equivalent to 30% and used in the experiment.

A syrup (RSS) containing rare sugars produced by alkali isomerization of an isomerized sugar (high-fructose corn syrup) which is a mixed sugar containing D-glucose and D-fructose as main compositions is a conversion type isomerized sugar containing D-psicose (5.4 g), D-sorbose (5.3 g), D-tagatose (2.0 g), D-allose (1.4 g), and B-mannose (4.3 g) in 100 g, and is a "food product" sold in common stores.

A malaria parasite growth blocking effect of a rare sugar was examined in the same manner as in Example 1 except that the second group (a mixed aqueous solution of 100 mM D-psicose and 440 mM D-fructose) in Example 1 was changed to a solution obtained by diluting Rare Sugar Sweet (RSS) 2.3 times with pure water. The results are shown in FIGS. 12 to 15.

FIG. 12 shows the results of counting the number of ookinetes in the midgut of the mosquito when one day passed after sucking blood. The suppression of the formation of ookinetes by Rare Sugar Sweet (diluted 2.3 times) is the same as the suppression by D-allose+fructose, and is slight.

10 days after sucking blood, that is, as a result of counting the number of oocysts formed by ookinetes penetrating the midgut, the number of oocysts in the D-allose+fructose feeding group was suppressed by 100% as compared with the control group, however, in the Rare Sugar Sweet (diluted 2.3 times) feeding group, the formation of oocysts was suppressed by 95.6% (FIG. 13). The number of sporozoites in the midgut 18 days after sucking blood was suppressed by 100% in the D-allose+D-fructose feeding group as compared with the control group, and suppressed by about 99.5% in the Rare Sugar Sweet (diluted 2.3 times) feeding group. On the other hand, the number of sporozoites in the salivary glands after 18 days, the same as above, was suppressed by 100% in both of the D-allose+fructose feeding group and the Rare Sugar Sweet (diluted 2.3 times) feeding group.

Example 6

Each of the *Anopheles stephensi* mosquitoes in the three groups fed with the feed for 20 days in the above Example 5 was made to suck blood of the BALE/c mice (6 weeks of age, female). In each group, 50 mosquitoes were made to suck blood of 5 mice for 1 minute 5 times for each mouse. Every day from 2 days after sucking blood, a smear preparation was prepared from a small amount of blood collected from the tail of each mouse, followed by Giemsa staining, and thereafter, the presence or absence of parasites was examined with a microscope. In some mice, parasites were confirmed 3 days after sucking blood, and thereafter, the incidence rate increased, however, whether or not malaria was developed was determined based on the presence or absence of parasites at the time point of 14 days after sucking blood in the end.

The results are shown in Table 4. In the control, the incidence rate was 100%, however, in the Rare Sugar Sweet (diluted 2.3 times) feeding group, malaria transmission was completely inhibited in the same manner as in the D-allose+D-fructose feeding group.

TABLE 4

Infectivity to Mice

| | Incidence rate after sucking blood (%) (mice which developed malaria/mice which had their blood sucked) |
|---|---|
| Fructose 440 mM | 100 (5/5) |
| Allose 100 mM + Fructose 440 mM | 0 (0/5) |
| Rare Sugar Sweet (diluted 2.3 times) | 0 (0/5) |

Surprisingly, the solution obtained by diluting Rare Sugar Sweet (RSS) 2.3 times showed a completely transmission-blocking effect in the same manner as the solution of 100 mM D-allose (+D-fructose). A notable result that the "food product" sold in common stores completely suppresses malaria transmission was obtained. Since a transmission-blocking effect was not observed in the case of "100 mM D-psicose+D-fructose", what interaction takes place is not known, however, RSS contains D-psicose (5.4 g), D-sorbose (5.3 g), D-tagatose (2.0 g), D-allose (1.4 g), and D-mannose (4.3 g) in 100 g, and therefore, the effect of RSS as a mixture may be an effect of a mixture of these rare sugars. Since a rare sugar is a "food product" sold in common stores, there would be a prospect for pursuing the possibility whether administration of a rare sugar can prevent malaria infection. By further studying the effect of increasing doses, elucidating the mechanism of action, it is expected that utilization of rare sugars as transmission-blocking agents will be acknowledged as an effective measures for malaria control.

INDUSTRIAL APPLICABILITY

Malaria which is one of the three major infectious diseases in the world causes about 200 million infected patients and 600, 000 deaths per year and is one of the most important tasks in global health. However, due to spread of drug-resistant parasites and insecticide-resistant mosquitoes, delays in the development of vaccines, and further, expansion of the habitat of a vector mosquito owing to global warming, etc., development of a new strategy is an urgent issue. The measure for a vector mosquito has been demanded to be changed from a conventional method which depends on an insecticide to a method which does not impose a burden on the human body or environment and does not use an insecticide. There has been no report, so far that a monosaccharide shows a growth inhibitory effect on a malaria parasite in the body of a mosquito by mixing the monosaccharide with a sugar liquid serving as a feed and making the mosquito suck the mixture.

By implementing the malaria transmission blocker and the malaria parasite growth inhibitor of the present invention, the risk of infection with malaria can be suppressed low even if a person is bitten by a malaria vector mosquito. This can suppress the harm of malaria regarded as the three major infectious diseases along with HIV/AIDS and tuberculosis low, and can contribute to protection of lives of people who live in endemic regions where about 40% of the world's population lives. A rare sugar serving as the active ingredient of the present invention exists in nature, and has an extremely low effect on the human body or nature, and does not disrupt the natural environment unlike insecticides, and therefore, provides a method for dealing with malaria which can be continuously applied to a vector mosquito over a long period of time in a wide range of regions.

The invention claimed is:

1. A method for inhibiting malaria parasite growth in the body of a mosquito, characterized by feeding a vector mosquito with an effective amount of D-allose, in addition to saccharides other than D-allose as a source of nutrient, to inhibit the malaria parasite growth in the body of the mosquito.

2. The method for inhibiting malaria parasite growth in the body of a mosquito according to claim 1, wherein the vector mosquito is fed with a solution of D-allose at a concentration of 10 mM to 100 mM.

3. The method for inhibiting malaria parasite growth in the body of a mosquito according to claim 1, wherein a stage in which a malaria parasite grows into any of an ookinete, an oocyst, and a sporozoite in the body of a mosquito is inhibited.

* * * * *